United States Patent
Bierl et al.

(10) Patent No.: US 8,935,950 B2
(45) Date of Patent: Jan. 20, 2015

(54) SENSOR FOR MEASURING HYDROCARBON CONTENT IN A FLOW OF GAS IN A PURGE LINE

(75) Inventors: Rudolf Bierl, Regensburg (DE); Philippe Grass, Regensburg (DE); Stephan Heinrich, Pfeffenhausen (DE); Manfred Weigl, Viehhausen (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 888 days.

(21) Appl. No.: 12/668,810

(22) PCT Filed: Sep. 3, 2007

(86) PCT No.: PCT/EP2007/059175
§ 371 (c)(1),
(2), (4) Date: Jan. 12, 2010

(87) PCT Pub. No.: WO2009/010102
PCT Pub. Date: Jan. 22, 2009

(65) Prior Publication Data
US 2010/0186482 A1    Jul. 29, 2010

(30) Foreign Application Priority Data

Jul. 13, 2007 (DE) .......................... 10 2007 033 144

(51) Int. Cl.
*G01N 7/00* (2006.01)
*F02M 25/08* (2006.01)
*F02D 41/00* (2006.01)
*G01N 27/18* (2006.01)

(52) U.S. Cl.
CPC ....... *F02M 25/0836* (2013.01); *F02D 41/0045* (2013.01); *F02D 2200/0611* (2013.01); *G01N 27/18* (2013.01); *G01N 2229/011* (2013.01); *G01N 2291/0215* (2013.01)
USPC .......................................................... 73/23.2

(58) Field of Classification Search
CPC .............. G01M 15/10; G01M 15/102; G01M 2291/0217
USPC ................................................ 73/23.2, 23.31
See application file for complete search history.

(56) References Cited

U.S. PATENT DOCUMENTS 5,372,047 A    12/1994    Russwurm et al.
(Continued)

FOREIGN PATENT DOCUMENTS

| DE | 40 10 148 A1 | 10/1991 |
|---|---|---|
| DE | 196 01 791 A1 | 7/1997 |
| DE | 100 57 342 A1 | 5/2002 |
| DE | 102005022121 | 11/2006 |

(Continued)

*Primary Examiner* — Peter Macchiarolo
*Assistant Examiner* — Alex Devito
(74) *Attorney, Agent, or Firm* — Cozen O'Connor

(57) ABSTRACT

A sensor for the measurement of the hydrocarbon content in a flow of gas in a purge line. The sensor can measure the hydrocarbon content in the flow of gas in the purge line from a hydrocarbon storage device to an internal combustion engine. The sensor has at least one heating element and at least one thermal detector, with the heating element heating the flow of gas while the thermal detector determines the temperature of the flow of gas, which temperature is evaluated as a measurement of the hydrocarbon content in the flow of gas.

13 Claims, 6 Drawing Sheets

(56) References Cited

U.S. PATENT DOCUMENTS

| | | |
|---|---|---|
| 5,390,644 A | 2/1995 | Nunogaki et al. |
| 6,227,177 B1 | 5/2001 | Yamafuji et al. |
| 6,474,138 B1 * | 11/2002 | Chang et al. .............. 73/31.05 |
| 6,662,121 B1 | 12/2003 | Oda et al. |
| 7,399,118 B2 | 7/2008 | Matter et al. |
| 2004/0099057 A1 * | 5/2004 | Hornung et al. .......... 73/204.26 |

FOREIGN PATENT DOCUMENTS

| | | |
|---|---|---|
| EP | 0 477 418 A1 | 4/1992 |
| EP | 1094306 | 4/2001 |
| EP | 1 391 703 B1 | 1/2007 |
| JP | 5-231209 A | 9/1993 |
| JP | 2006-57510 A | 3/2006 |
| WO | WO 01/18500 A1 | 3/2001 |

* cited by examiner

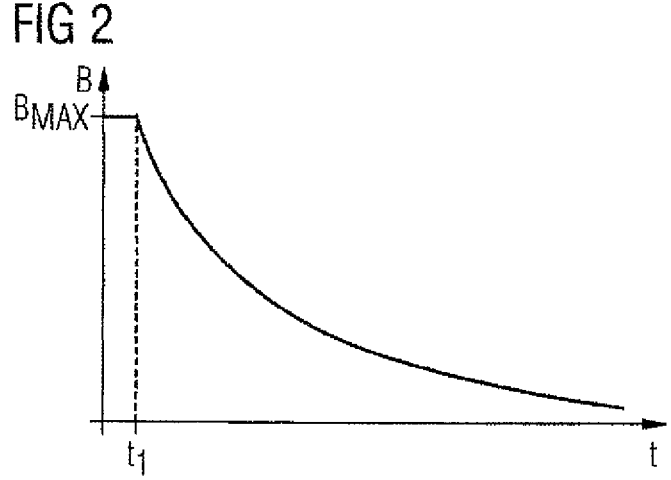
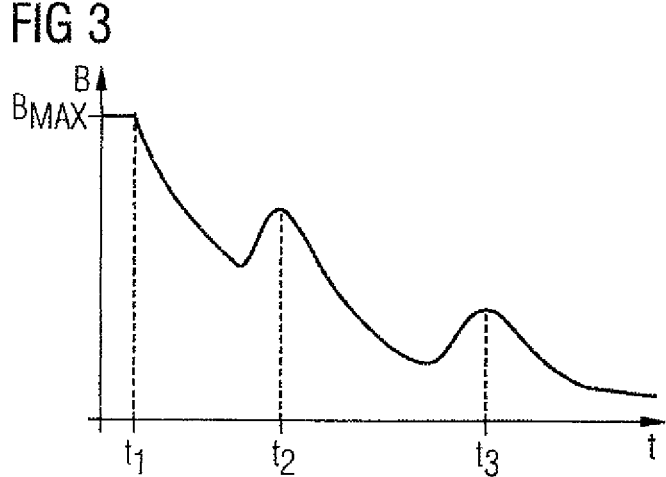
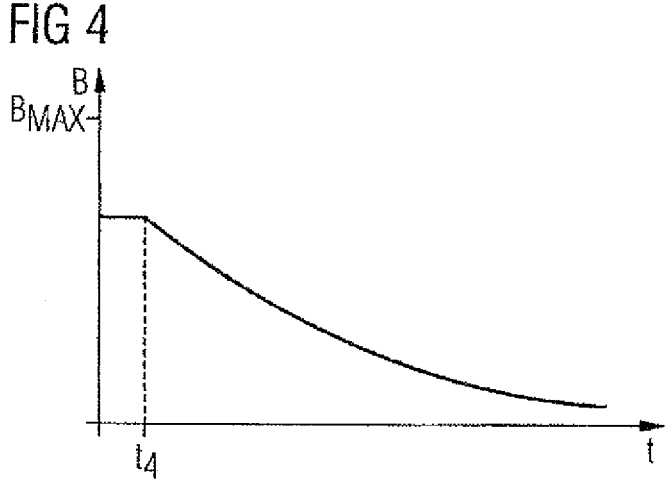

SENSOR FOR MEASURING HYDROCARBON CONTENT IN A FLOW OF GAS IN A PURGE LINE

PRIORITY CLAIM

This is a U.S. national stage of application No. PCT/EP2007/059175, filed on Sep. 3, 2007 which claims priority to the German Application No.: 10 2007 033 144.6, Filed: Jul. 13, 2007; the content of both incorporated herein by reference.

BACKGROUND OF THE INVENTION

1. Field of the Invention

The invention relates to a sensor for measuring hydrocarbon content in a gas stream in a scavenging or purging line.

2. Prior Art

A central objective in the development of modern motor vehicles is to reduce the exhaust gases which are output by the motor vehicle. In the last few years, efforts have mainly concentrated on the cleaning of the combustion gases. However, there are also a series of further sources for undesired exhaust gases in motor vehicles. These sources include the fuel tank of the motor vehicle. Fuels such as, for example, premium gasoline which are stored in the fuel tank contain a series of highly volatile hydrocarbons. These include, for example, methane, butane, and propane. These low-viscosity hydrocarbons can become released from the fuel, when there are high external temperatures in the summer or as a result of the fuel being shaken during travel, and can leave the fuel tank as a gaseous component. To counteract this, modern fuel tanks are sealed off from the outside in a gas-tight fashion. The volatile hydrocarbons must then be buffered in a hydrocarbon accumulator. Such hydrocarbon accumulators are small tanks, which are arranged above or on the fuel tank and contain, for example, an activated carbon storage element. The vaporized hydrocarbons are taken up by the activated carbon, stored and discharged again when necessary. After the activated carbon accumulator has taken up a certain quantity of the hydrocarbons, the hydrocarbon accumulator is emptied via a scavenging line. For this purpose, external air is blown into the hydrocarbon accumulator, which air takes up the hydrocarbons and carries them from the hydrocarbon accumulator to the internal combustion engine via the scavenging line. The hydrocarbons can then be fed into the intake air of the internal combustion engine and therefore contribute to the combustion. Since a certain quantity of energy is already fed to the internal combustion engine as a result of the hydrocarbons in the intake air, the injection system should inject correspondingly less fuel. According to the prior art, the valve in the scavenging line is opened according to a model stored in the engine controller, with the fuel/air mixture in the internal combustion engine being correspondingly enriched, and corresponding adjustment of the injected fuel is aimed at by means of a λ probe in the exhaust train. This control by the λ probe occurs relatively slowly, with the result that when the valve in the scavenging line opens according to the model stored in the engine controller, an air/fuel mixture which is significantly too rich is usually burnt in the engine. This leads to increased consumption by the internal combustion engine and to very poor exhaust gas values. Particularly in hybrid vehicles with very low exhaust gas emission and an internal combustion engine, which is often stationary, the problem occurs of the controlled scavenging of the hydrocarbon accumulator.

SUMMARY OF THE INVENTION

An object of the present invention is to provide a sensor that can precisely measure hydrocarbon content in the gas stream in a scavenging line from a hydrocarbon accumulator to an internal combustion engine.

The sensor has at least one heating element and at least one temperature probe, wherein the heating element heats the gas stream and the temperature probe determines the temperature of the gas stream, which temperature is evaluated as a measure of the hydrocarbon content in the gas stream, the hydrocarbon content in the gas stream in the scavenging line can be sensed very precisely. The invention is based on the realization that the function f(X)=STP(DTP) differs significantly for different gases and gas mixtures (hydrocarbon content in the gas mixture), and this can be represented very well with characteristic diagrams. The hydrocarbon content in the gas stream in the scavenging line can be determined by these characteristic diagrams and with the measured values of the sensor.

In one embodiment of the invention, the hydrocarbon accumulator is an accumulator, which is filled with activated carbon. Activated carbon stores the hydrocarbons very effectively and is economical and environmentally compatible.

In one embodiment of the invention, a first temperature probe is arranged upstream of the heating element in the gas stream and a second temperature probe is arranged downstream of the heating element in the gas stream. The sensing of the gas properties is therefore particularly precise.

In one embodiment of the invention, the temperature difference is determined between the second temperature probe and the first temperature probe. The temperature difference forms the thermal conductivity capacity of the gas mixture.

The temperature sum is determined between the first temperature probe and the second temperature probe. The temperature sum forms the thermal conductivity of the gas mixture.

In one embodiment of the invention, the mass flow rate of the hydrocarbons in the scavenging line is determined from the temperature difference and the temperature sum. Using the corresponding characteristic diagrams makes this a simple and rapid computing operation, which can be carried out by the electronic engine controller or a processor on the sensor.

In one embodiment of the invention, the volume flow rate of the hydrocarbons in the scavenging line is determined from the temperature difference and the temperature sum. The volume flow rate of the hydrocarbons is an important variable for calculating the composition of the fuel/air mixture. The determination of the mass flow rate and of the particle flow rate of hydrocarbons in the scavenging line is highly significant for the calculation of the composition of the fuel/air mixture.

Furthermore, it is advantageous if the sensor in or on the scavenging line is arranged in or on the hydrocarbon accumulator and/or in or on the intake section. The use of a plurality of sensors at various previously mentioned positions may be perfectly appropriate to obtain a particularly precise measurement.

In one embodiment of the invention, the sensor has at least one ultrasonic source and at least one ultrasonic receiver, wherein the propagation time of an ultrasonic pulse which is transmitted from the ultrasonic source through the gas stream to the ultrasonic receiver is evaluated as a measure of the hydrocarbon content in the gas stream, it is also possible to sense the hydrocarbon content in the gas stream in the scavenging line very precisely. The invention is also based here on the realization that the function f(X)=StauP(DtauP) for different gases and gas mixtures (hydrocarbon content in the gas mixture) differs significantly, and this can be represented very well with characteristic diagrams. The hydrocarbon content in the gas stream in the scavenging line can be determined without difficulty by means of these characteristic diagrams and with the measured values of the sensor.

In one embodiment of the invention, the ultrasonic source is embodied simultaneously as an ultrasonic receiver. As a result, ultrasonic pulses can be very easily transmitted along with the gas stream and counter to the gas stream.

In one embodiment of the invention, the difference between the propagation time from the first ultrasonic transmitter to the second ultrasonic receiver and the propagation time from the second ultrasonic transmitter to the first ultrasonic receiver is determined. This difference in propagation time correlates with the speed of the gas stream.

Furthermore, in one embodiment of the invention the sum of the propagation time from the first ultrasonic transmitter to the second ultrasonic receiver and the propagation time from the second ultrasonic transmitter to the first ultrasonic receiver is determined. The sum propagation time correlates with the speed of sound in the gas mixture transported in the gas stream.

In one embodiment of the invention, the hydrocarbon content in the gas stream in the scavenging line is determined from the difference between the propagation times and the sum of the propagation times by utilizing a characteristic diagram. Using the corresponding characteristic diagrams makes this an easy and rapid computing operation which can be carried out by the electronic engine controller or the processor on the sensor.

In one embodiment of the invention, the volume flow rate of the hydrocarbons in the scavenging line is determined from the difference between the propagation times and the sum of the propagation times. The volume flow rate of the hydrocarbons is an important variable for calculating the composition of the fuel/air mixture. The determination of the mass flow rate and of the particle flow rate of hydrocarbons in the scavenging line is highly significant for the calculation of the composition of the fuel/air mixture.

BRIEF DESCRIPTION OF DRAWINGS

Embodiments of the invention are illustrated by way of example in the figures, in which:

FIG. 2 is a graph of an ideal discharge behavior of the hydrocarbon accumulator;

FIG. 3 is a graph of a real emptying behavior of the hydrocarbon accumulator,

FIG. 4 is a graph of an emptying behavior of the hydrocarbon accumulator, which is only partially filled;

DETAILED DESCRIPTION OF THE PREFERRED EMBODIMENTS

Figure 1:
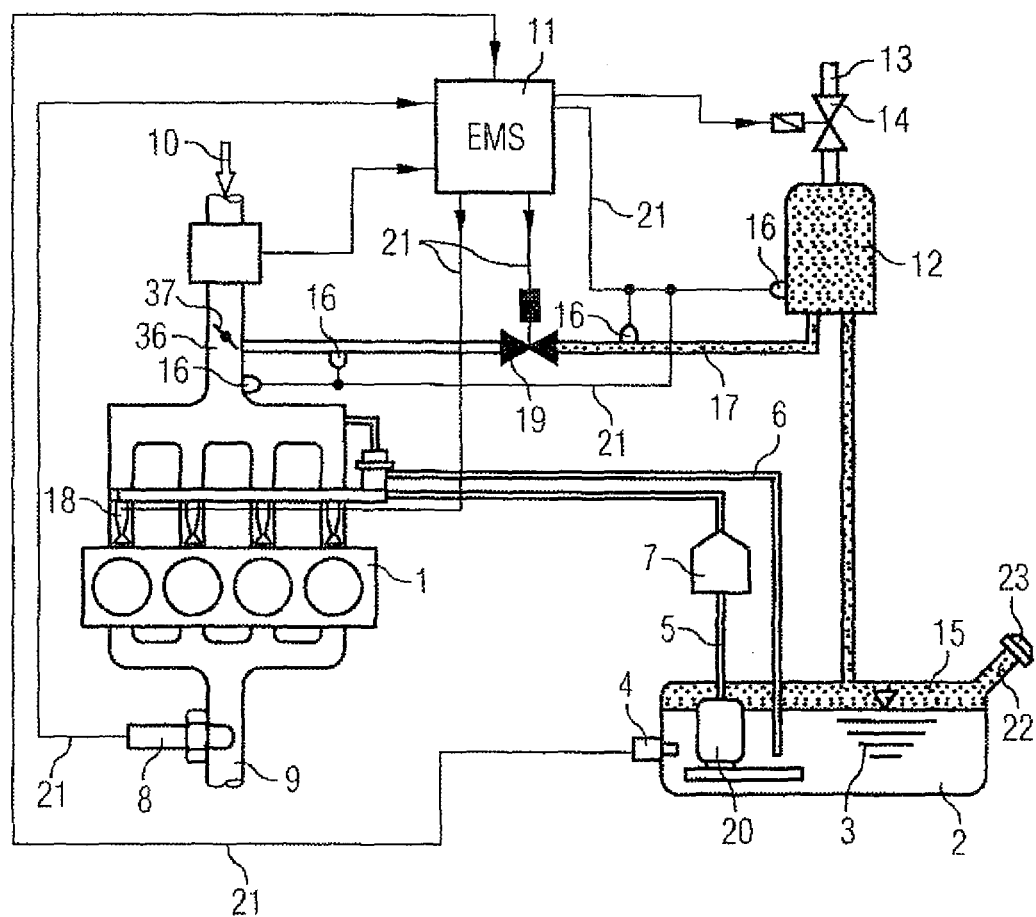
FIG. 1 is a an internal combustion engine with its fuel supply.

FIG. 1 shows an internal combustion engine 1 which is connected to a fuel tank 2 by a fuel line 5. A fuel feeder unit 20 in the fuel tank 2 feeds fuel 3 via the fuel line 5 and a fuel filter 7 to the internal combustion engine 1 where the fuel 3 is injected into an intake section 36 with injection valves 18 and is burnt in the internal combustion engine 1. The exhaust gases of the combustion process are conveyed away from the engine through an exhaust section 9. A λ probe 8, which monitors the exhaust gases and is intended to permit optimum combustion of the fuel/air mixture, can be seen in the exhaust section 9. For this purpose, the λ probe 8 is connected via an electrical signal line 21 to an electronic engine controller (EMS) 11. Furthermore, an air inlet 10, which leads to the intake section 36 in which a throttle valve 37 is arranged, can be seen in FIG. 1.

Fuel 3 can be seen in the fuel tank 2. In order to differentiate various fuel qualities, a sensor 4 for detecting the fuel composition is arranged in the fuel tank 2. This may be, for example, a flex fuel sensor. As a result of a high ambient temperature it is possible for low-viscosity hydrocarbons to evaporate from the fuel 3. This results in a gas mixture 15 with hydrocarbons above the fuel 3 in the fuel tank 2. Since the fuel tank 2 is hermetically sealed off from the outside at the end of its filler neck 22 by a filler cap 23, an excess pressure is produced in the fuel tank 2, which excess pressure causes the vaporized hydrocarbons to be forced into a hydrocarbon accumulator 12. This hydrocarbon accumulator 12 can take up only a certain quantity of hydrocarbons until it becomes saturated. If the hydrocarbon accumulator 12 is saturated with hydrocarbons, the hydrocarbon accumulator 12 must be purged. To do this, a scavenging valve 14 is opened and air is pumped into the hydrocarbon accumulator 12 via a scavenging air inlet 13, which air takes up the hydrocarbons and conveys them to the internal combustion engine 1, via a scavenging line 17. To do this, a scavenging line valve 19 is opened. The electronic engine controller 11 is configured to open the scavenging line valve 19.

The emptying of the hydrocarbon accumulator 12 is illustrated in FIGS. 2 to 4 in which it is apparent that the emptying does not in any way always have to take place according to a model stored in the electronic engine controller 11. In particular, FIGS. 3 and 4 show that the emptying behavior of the hydrocarbon accumulator can differ from the ideal model, which is illustrated in FIG. 2. It is therefore extremely difficult to control the scavenging line valve 19 precisely only with a model stored in the electronic engine controller 11 so that over-enrichment of the fuel/air mixture cannot occur in the internal combustion engine 1.

To bring about optimum emptying of the hydrocarbon accumulator 12, sensors 16 for detecting the hydrocarbon content B in the scavenging line 17 are formed in or on the hydrocarbon accumulator 12, in or on the scavenging line 17 or in or on the intake section 36. These sensors 16 can be used to detect the hydrocarbon content B in the gas stream 31 FIG. 8 of the scavenging line 17 with high precision. Based on these measured values, the electronic engine controller 11 can set an optimum fuel/air mixture in the combustion chambers of the internal combustion engine 1 by simply adding a smaller quantity of fuel 3 to the air/gas mixture via the injection valves 18 when the gas stream 31 (FIG. 8) is heavily loaded with hydrocarbons. It therefore becomes very easy for the λ probe 8 to set an optimum λ=1, which ensures low-pollutant combustion of the hydrocarbons in the internal combustion engine 1.

It is to be noted that the existing quality of the fuel 3 can be detected by the flex fuel sensor 4, as a result of which the corresponding characteristic diagram, from which the hydrocarbon content in the scavenging line 17 can be inferred with the data of the sensor 16, can be loaded into the electronic engine controller 11. Various characteristic diagrams for various fuel qualities should be stored in the electronic engine controller 11 for this purpose.

FIG. 2 is an ideal emptying behavior for the hydrocarbon accumulator 12. Assuming that the hydrocarbon accumulator 12 is saturated completely with hydrocarbons by the time $t_1$, the scavenging air valve 14 and the scavenging line valve 19 are opened by the engine controller 11 at the time $t_1$. Scavenging air penetrates the completely saturated hydrocarbon accumulator through the scavenging air inlet 13 and takes up the hydrocarbons, which are fed to the internal combustion engine 1. In an ideal case, the emptying of the hydrocarbon accumulator 12 takes place decreasing exponentially over time. The content B of hydrocarbons in the gas stream 31 approaches the value 0 over time. After the scavenging line valve 19 opens, a very large quantity of hydrocarbons initially flows to the internal combustion engine 1, wherein this quantity converges decreasing exponentially toward B=0. Under real conditions, external influences, for example shocks to the motor vehicle during travel as a result of potholes or other unevennesses, lead to a significantly different emptying behavior of the hydrocarbon accumulator 12.

This real emptying behavior is illustrated in FIG. 3. Assuming again a completely saturated hydrocarbon accumulator 12, the emptying of the hydrocarbon accumulator 12 starts at the time $t_1$ with the opening of the scavenging air valve 14 and of the scavenging line valve 19. Initially, the known exponential decrease in the content B of the hydrocarbons starts in the gas stream 31 of the scavenging line 17. At the time $t_2$, the hydrocarbon accumulator 12 experiences a shock, for example due to the vehicle travelling over a pothole. The content B of the hydrocarbons in the gas stream 31 increases suddenly. After this event, the content B of the hydrocarbons in the gas stream 31 decreases again exponentially, with a further shock event on the hydrocarbon accumulator 12 occurring at the time $t_3$, which shock event leads again to increased outputting of hydrocarbons to the gas stream 31. This so-called "coughing up" of the hydrocarbon accumulator 12 leads to a content B of the hydrocarbons in the gas stream 31 which differs greatly from the ideal characteristic curve (FIG. 2). Without corresponding control with a sensor 16 for detecting the hydrocarbon content B in the gas stream 31, the coughing up would lead to temporary over-enrichment of the fuel/air mixture and therefore to combustion exhaust gases, which were highly loaded with pollutants.

A further scenario for the emptying of the hydrocarbon accumulator 12 is illustrated in FIG. 4. It is not possible in any way to always assume that the hydrocarbon accumulator 12 is completely saturated with hydrocarbons at the time of the opening of the scavenging air valve 14 and of the scavenging line valve 19. As a result, the exponential decrease in the content B of the hydrocarbons in the gas stream turns out completely differently since the engine is operating in a completely different range of the exponential function. At the time $t_4$, the scavenging air valve 14 and the scavenging line valve 19 are opened with the hydrocarbon accumulator 12 partially loaded, and it can be clearly seen that the function converges toward 0 in a much flatter way than in the example in FIG. 2.

FIGS. 3 and 4 make it clear that for an optimum fuel/air mixture in the internal combustion engine 1 it is indispensible to measure the content B of the hydrocarbons in the gas stream 31 of the scavenging line 17 precisely.

Figure 5:
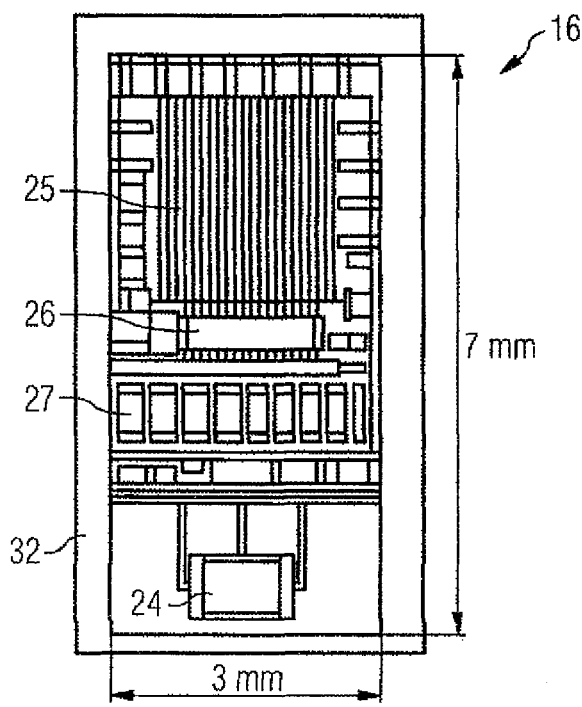
FIG. 5 is a sensor for detecting the hydrocarbon content according to one embodiment of the invention.

FIG. 5 is the sensor 16 for detecting the hydrocarbon content B in the gas stream 31 in a scavenging line 17 from hydrocarbon accumulator 12 to internal combustion engine 1. The sensor 16 is embodied here as a micromechanical component which is integrated on a silicon chip 32. It is possible to see the evaluation circuit 25, which can be embodied as a microprocessor, and an EPROM 26. Furthermore, the sensor 16 for detecting the hydrocarbon content B contains an analog/digital converter (ADC) 27 which converts the analog signals of the sensor element 24 into digital signals which can be processed by the evaluation circuit 25. The micromechanical sensor 16 for detecting the hydrocarbon content has an extent of approximately 3 mm times 7 mm.

Figure 6:
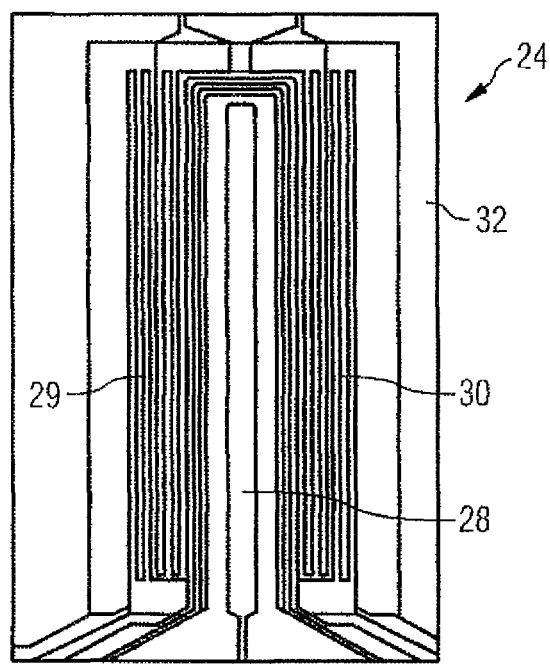
FIG. 6 is a sensor element.

The actual sensor element 24 is illustrated in FIG. 6, which shows the sensor element 24 with a first temperature probe 29 and a second temperature probe 30. The heating element 28 is arranged between the first temperature probe 29 and the second temperature probe 30. These elements are integrated on the silicon chip 32. The gas stream 31 which flows past the sensor element 24 is heated by the heating element 28 in a defined fashion. The first temperature probe 29 is arranged upstream of the heating element 28 and it senses the temperature of the gas stream 31 upstream of the heating element 28, and the second temperature probe 30 is arranged downstream of the heating element 28 and it senses the temperature of the heated gas stream 31. If these temperatures are added together, the sum temperature STP is acquired. If the difference between the temperatures is formed, the differential temperature DTP is acquired. The sum temperature STP stands for the property of the thermal conductivity in the medium flowing past, the differential temperature DTP stands for the property of the thermal capacity of a gas mixture flowing past. From these two values (STP and DTP) it is possible to determine the mass flow rate of the medium flowing past and, by using a characteristic diagram such as the one illustrated in FIG. 9, to determine the content B of hydrocarbons in the gas stream 31 in the scavenging line 17. The procedure for determining the content B of hydrocarbons in the gas stream 31 will be explained later in more detail in conjunction with FIG. 9.

Figure 7:
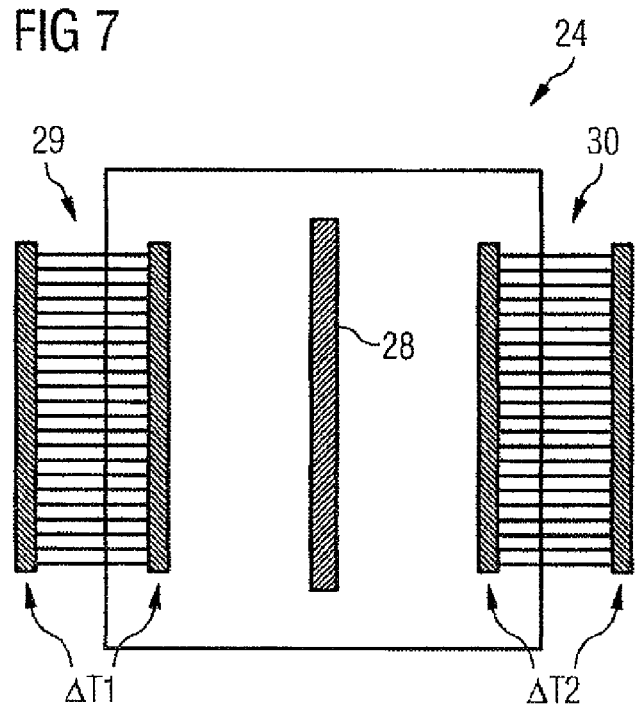
FIG. 7 is a further representation of the sensor element.

FIG. 7 shows a further illustration of the sensor element 24 with a first temperature probe 29 and a second temperature probe 30 as well as a heating element 28. The first temperature probe 29 is composed of two temperature probes, which can measure a temperature difference $\Delta T_1$, and also the second temperature probe 30 is composed of two temperature probes which can measure a second temperature difference $\Delta T_2$. The overall temperature difference is then obtained as the difference $\Delta T_2 - \Delta T_1$. This sensor element 24 also senses the temperatures upstream and downstream of the heating element 28. For a specific gas, a permanently determined ratio of $\Delta T_1 + \Delta T_2$ is obtained as $\Delta T_2 - \Delta T_1$ given a specific mass flow rate. If the gases contained in the gas mixture are known, which is ensured by the flex fuel sensor 4, it is possible, for example, for the electronic engine controller 11 or the microprocessor 25 in the sensor 16 to calculate both the mass flow rate and the gas composition. To do this, the evaluation circuit accesses a series of characteristic diagrams stored in the electronic engine controller 11 and selects the most relevant one for the detected fuel. The temperature difference $\Delta T_2 - \Delta T_1$ reacts here to the thermal capacity of the gas mixture, and the sum $\Delta T_1 + \Delta T_2$ reacts more to its thermal conductivity. The characteristic curve of air and that of air which, has been enriched with hydrocarbon, differ markedly so that even small concentrations of hydrocarbon in the air give rise to a significantly different characteristic curve. As a result, the sensor 16 can be used to control the aperture cross section of the scavenging line valve 18 very precisely, so that optimum mixture formation occurs in the internal combustion engine 1.

Figure 8:
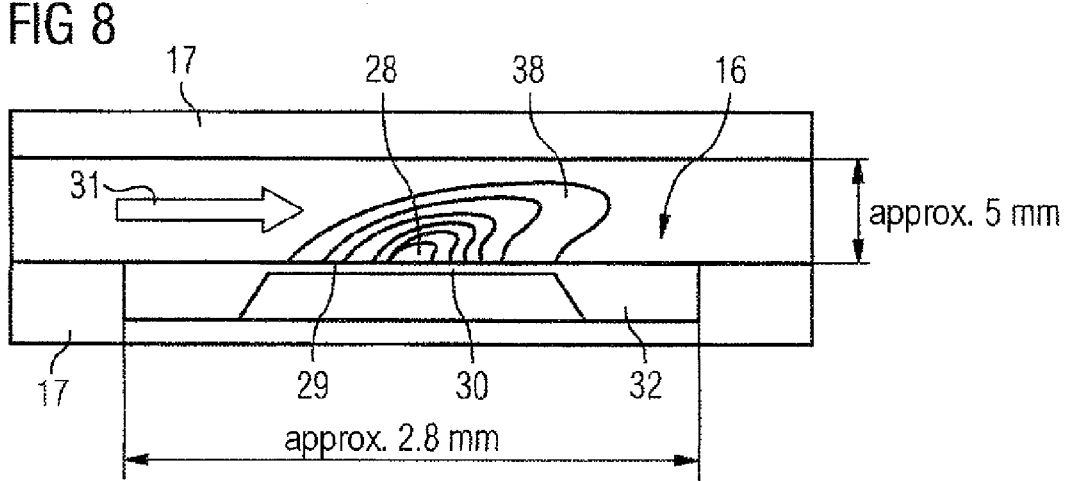
FIG. 8 is the sensor for detecting the hydrocarbon content in its installation situation in a scavenging line.

FIG. 8 shows the sensor 16 for detecting the hydrocarbon content B in its installation position in the scavenging line 17. The gas stream 31 is indicated by the arrow. The sensor 16 contains the heating element 28 and the temperature probes 29, 30 which are arranged upstream and downstream of the heating element 28. The entire sensor 16 is arranged on a silicon chip 32, and the silicon chip 32 is integrated into the pipe wall of the scavenging line 17. Isotherms 38, which are intended to represent the temperature gradient by the temperature probes 29 and 30, can be seen by the heating element 28. From the sum of the sensed temperatures STP and the difference between the sensed temperatures DTP it is possible to infer the content B of hydrocarbons in the gas stream 31. FIG. 8 is not drawn to scale but in order to clarify the dimensions the cross section of a customary scavenging line 17 is specified as approximately 5 mm and the extent of the silicon chip 32 is approximately 2.8 mm.

Figure 9:
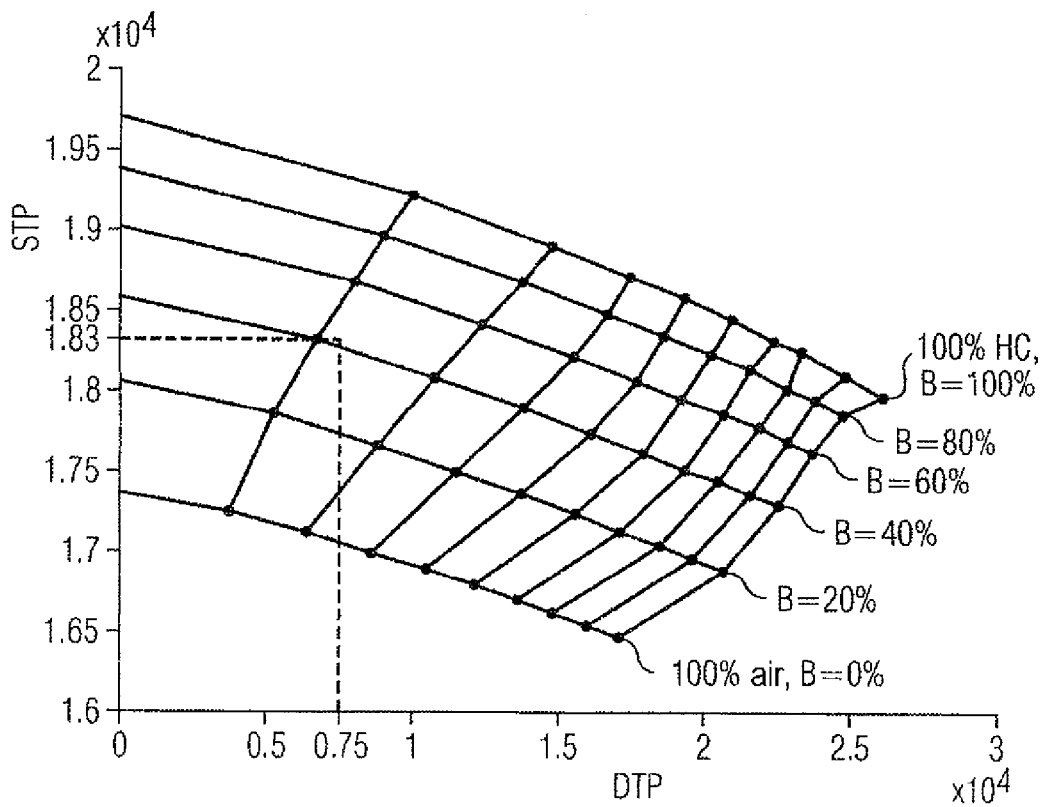
FIG. 9 is a characteristic diagram for evaluating the measurement results of the sensor.

The invention is based on the realization that the function f(X)=STP(DTP) differs significantly for different gases and gas mixtures (hydrocarbon content B in the gas mixture), and this can be seen in the characteristic diagram in FIG. 9.

FIG. 9 then shows the characteristic diagram for evaluating the measurement results of the sensor 16 for detecting the hydrocarbon content B in the gas mixture. The differential temperature DTP composed of the temperature T2 of the second temperature probe 30 and the temperature T1 of the first temperature probe 29 is plotted on the X axis (DTP=$T_2$−$T_1$ or according to FIG. 7 DTP=$\Delta T_2$−$\Delta T_1$). The sum temperature STP of the first temperature probe 29 and of the second temperature probe 30 is plotted on the Y axis of the diagram in FIG. 9 (STP=$T_2$+$T_1$ or, according to FIG. 7, STP=$\Delta T_2$+$\Delta T_1$). The entire characteristic diagram in FIG. 9 has been determined for a specific fuel, for example premium gasoline, and is stored in the engine controller 11. If the sensor 16 detects a specific differential temperature DTP and a specific sum temperature STP, the intersection of these two values in the characteristic diagram gives rise to a specific line (f(x)= STP(DTP)) which correlates with a content B of hydrocarbons in the gas stream. If the sensor 16 measures, for example, a differential temperature DTP of 0.75*$10^4$ and a sum temperature of STP of 1.83*$10^4$, an intersection point of the two values occurs in the characteristic diagram at a content B of 40% hydrocarbon in the gas stream 31 in the scavenging line 17. In this way, the sensor 16 can be used to determine the content of hydrocarbon in the scavenging line 17 very precisely.

Figure 10:
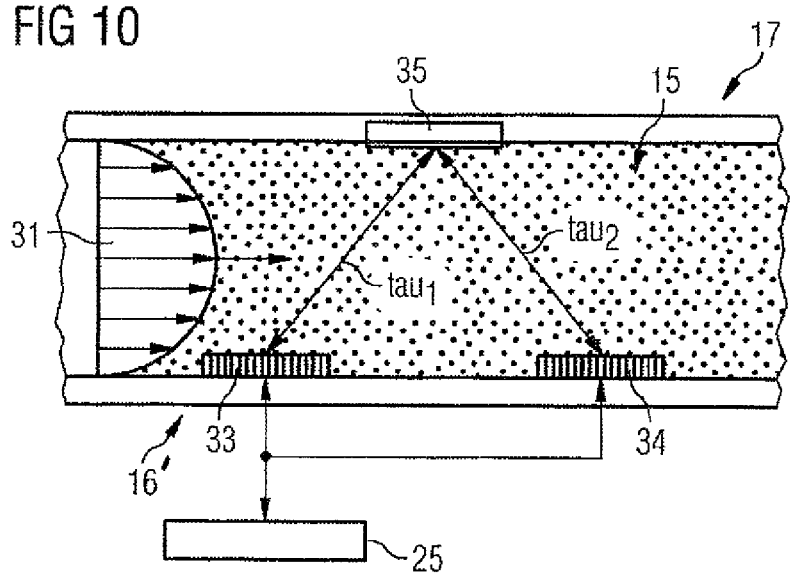
FIG. 10 is another embodiment of the sensor for detecting the hydrocarbon content.

FIG. 10 is an alternative embodiment of the sensor 16' for detecting the hydrocarbon content B. The scavenging line 17 is shown again with the gas mixture 15 flowing therein with hydrocarbons. In the case of this sensor 16' for detecting the hydrocarbon content B, a first ultrasonic source 33 is formed, which can also serve as an ultrasonic receiver 33, and a second ultrasonic source 34 is formed, which can also serve as an ultrasonic receiver 34. In addition, it is possible to see a sound reflector 35. The sound reflector 35 is, however, not absolutely necessary for the implementation of the invention, and the ultrasonic sources and ultrasonic receivers 33, 34 can also be arranged opposite one another. An ultrasonic pulse is emitted by the first ultrasonic source 33 and transmitted via the ultrasonic reflector 35 to the second ultrasonic receiver 34. The propagation time tau1, which is required in this context, is registered by the evaluation circuit 25. After the ultrasonic pulse has passed from the first ultrasonic source 33 via the sound reflector 35 to the second sound receiver 34, the second ultrasonic receiver is then used as a second sound source 34 and likewise emits an ultrasonic pulse which runs counter to the gas stream 31 via the sound reflector 35 to the first sound receiver 33 and requires a propagation time tau2 for this. A sum propagation time StauP=tau1+tau2 and a differential propagation time DtauP=tau2−tau1 can also be formed here from the propagation times between the ultrasonic sources and ultrasonic receivers. The sum propagation time StauP correlates here with the speed of sound in the gas mixture 15, and the differential propagation time DtauP correlates with the speed of the medium. The determination of the content B of hydrocarbons in the gas stream 31 in the scavenging line is then carried out in a way analogous to the situation with the sensors described in FIGS. 5 to 8.

Figure 11:
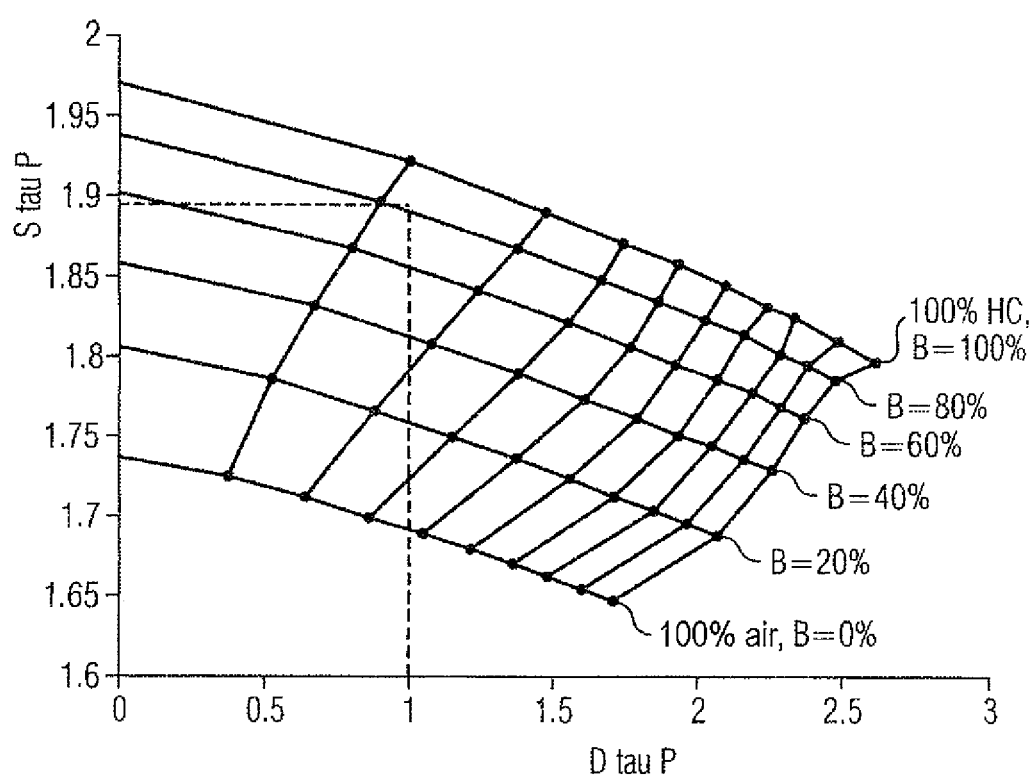
FIG. 11 is a characteristic diagram for the sensor according to FIG. 10.

The invention is also based here on the realization that the function f(X)=StauP(DtauP) differs significantly for different gases and gas mixtures (hydrocarbon content B in the gas mixture) and this can be clearly seen in the characteristic diagram in FIG. 11. Only the differential propagation time DtauP=tau2−tau1 is represented on the X axis in FIG. 11, and the sum propagation time StauP=tau1+tau2 is represented on the Y axis.

If both propagation times are measured with the sensor 16 according to FIG. 10, it is possible to infer the content B of hydrocarbons in the gas stream 31 in the characteristic diagram according to FIG. 11. An example of this is a differential propagation time DtauP=1 in relative units, and a sum propagation time DTP=1.9 in relative units. If these two values are combined in the characteristic diagram, a curve is obtained which represents a content B of hydrocarbons in the gas stream of 80%. The content B of hydrocarbons in the gas stream 31 of the scavenging line 17 can also be determined very precisely with the sensor 16 illustrated in FIG. 10. The characteristic diagram according to FIG. 11 is in turn produced for a specific fuel and stored in the electronic engine controller 11. The flex fuel sensor 4 then detects the composition of the fuel 3 in the tank 2, as a result of which the electronic engine controller 11 can always make available the characteristic diagram which is suitable for the fuel used.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:
1. A scavenging line/sensor assembly comprising:
a scavenging line leading from a hydrocarbon accumulator to a combustion engine;
a sensor configured to measure a hydrocarbon content in a gas stream in said scavenging line, said sensor comprising:

at least one heating element configured to heat the gas stream; and at least one temperature probe configured to determine a temperature of the heated gas stream comprising:

a first temperature probe arranged upstream of the heating element in the gas stream configured to measure a first temperature difference; and a second temperature probe arranged downstream of the heating element in the gas stream configured to measure a second temperature difference, wherein the measured hydrocarbon content in the gas stream is based on the determined temperature differences, wherein each of the first and the second temperature probes comprises two temperature probes, wherein the first temperature probe determines a first temperature difference upstream of the heating element in the gas stream; and the second temperature probe determines a second temperature difference arranged downstream of the heating element in the gas stream, whereby a temperature difference between the first and second temperature differences corresponds to a thermal capacity of the gas stream and a temperature sum of the first and second temperature differences corresponds to a corresponds to a thermal conductivity of the gas stream.

2. The scavenging line/sensor assembly as claimed in claim 1, wherein the hydrocarbon accumulator is configured as an accumulator filled with activated carbon.

3. The scavenging line/sensor assembly as claimed in claim 1, wherein the hydrocarbon content in the gas stream in the scavenging line is determined utilizing a characteristic diagram based on the temperature difference and the temperature sum.

4. The scavenging line/sensor assembly as claimed in claim 1, wherein a mass flow rate of the hydrocarbon content in the gas stream in the scavenging line is determined based on the temperature difference and the temperature sum.

5. The scavenging line/sensor assembly as claimed in claim 1, wherein a volume flow rate of the hydrocarbons in the scavenging line is determined based on the temperature difference and the temperature sum.

6. The scavenging line/sensor assembly as claimed in claim 1, wherein a particle flow rate of the hydrocarbons in the scavenging line is determined based on the temperature difference and the temperature sum.

7. A hydrocarbon accumulator comprising:

a scavenging line leading from the hydrocarbon accumulator to a combustion engine;

a sensor configured to measuring a hydrocarbon content in a gas stream in the scavenging line, the sensor comprising at least one heating element configured to heat the gas stream and at least one temperature probe configured to determine a temperature difference of the heated gas stream, a first temperature probe upstream of the at least one heating element and a second temperature probe downstream of the at least one heating element, wherein each of the first and second temperature probes comprises two temperature probes, wherein the first temperature probe determines a first temperature difference upstream of the heating element in the gas stream; and the second temperature probe determines a second temperature difference arranged downstream of the heating element in the gas stream, whereby a temperature difference between the first and second temperature differences corresponds to a thermal capacity of the gas stream and a temperature sum of the first and second temperature differences corresponds to a corresponds to a thermal conductivity of the gas stream, and whereby the measured hydrocarbon content in the gas stream is based on the determined temperature difference by measuring the gas stream upstream and downstream of the at least one heating element.

8. The hydrocarbon accumulator as claimed in claim 7, wherein the hydrocarbon accumulator is configured as an accumulator filled with activated carbon.

9. The hydrocarbon accumulator as claimed in claim 7, wherein a temperature sum is determined between the first temperature probe and the second temperature probe.

10. The hydrocarbon accumulator as claimed in claim 7, wherein the hydrocarbon content in the gas stream in the scavenging line is determined utilizing a characteristic diagram based on the temperature difference and the temperature sum.

11. The hydrocarbon accumulator as claimed in claim 7, wherein a mass flow rate of the hydrocarbon content in the gas stream in the scavenging line is determined based on the temperature difference and the temperature sum.

12. The hydrocarbon accumulator as claimed in claim 7, wherein a volume flow rate of the hydrocarbons in the scavenging line is determined based on the temperature difference and the temperature sum.

13. The hydrocarbon accumulator as claimed in claim 7, wherein a particle flow rate of the hydrocarbons in the scavenging line is determined based on the temperature difference and the temperature sum.

* * * * *